United States Patent [19]

Goldwasser

[11] Patent Number: 5,709,747
[45] Date of Patent: Jan. 20, 1998

[54] COATING SELECTIVE ZONES OF THIN WEBS TO CHANGE THE PERVIOUS CHARACTER THEREOF, USING A COVER

[75] Inventor: Moshe Goldwasser, Tel Aviv, Israel

[73] Assignee: Avgol Nonwoven Industries, Israel

[21] Appl. No.: 434,672

[22] Filed: May 5, 1995

Related U.S. Application Data

[63] Continuation-in-part of Ser. No. 232,692, Apr. 25, 1994, abandoned.

[51] Int. Cl.$^6$ .................. B05C 11/00; B05C 1/06
[52] U.S. Cl. .................. 118/211; 118/246; 118/258; 118/263
[58] Field of Search .................. 118/235, 244, 118/248, 246, 211, 263; 427/209–211, 501, 504, 288, 194, 428; 156/472, 473, 494, 390, 553

[56] References Cited

U.S. PATENT DOCUMENTS

| | | | |
|---|---|---|---|
| 3,751,281 | 8/1973 | Peterson et al. | 427/428 |
| 3,931,786 | 1/1976 | Teed | 118/235 |
| 4,347,269 | 8/1982 | Keep | 427/428 |
| 4,748,044 | 5/1988 | Fottinger et al. | 427/44 |

*Primary Examiner*—Donald E. Czaja
*Assistant Examiner*—Calvin Padgett
*Attorney, Agent, or Firm*—Breiner & Breiner

[57] ABSTRACT

The process and apparatus of the present invention teaches how to treat a well-integrated woven or non-woven web of hydrophobic fibers to make selective areas hydrophyllic. It also can be used to make a web of hydrophyllic fibers selectively hydrophobic. It uses a plurality of selectively adjustable covers on an applicator roll rotating in a bath of liquid to place the liquid material on selective areas of the moving web. In a preferred embodiment the web is non-woven and the fibers are hydrophobic in nature, e.g., dry-laid or melt-blown polypropylene or polyethylene fibers or spun-bonded hydrophobic filaments. A woven web made of cotton or other hydrophyllic fibers may also be used if the end result is to create partially hydrophobic areas on a hydrophyllic web. The areas of liquid are positioned on the web only where desired so as to eliminate the excessive cost of unwanted and unnecessary coating material. If the web is hydrophobic, the liquid makes that area hydrophyllic. If the web is hydrophyllic, the liquid makes that area hydrophobic.

6 Claims, 3 Drawing Sheets

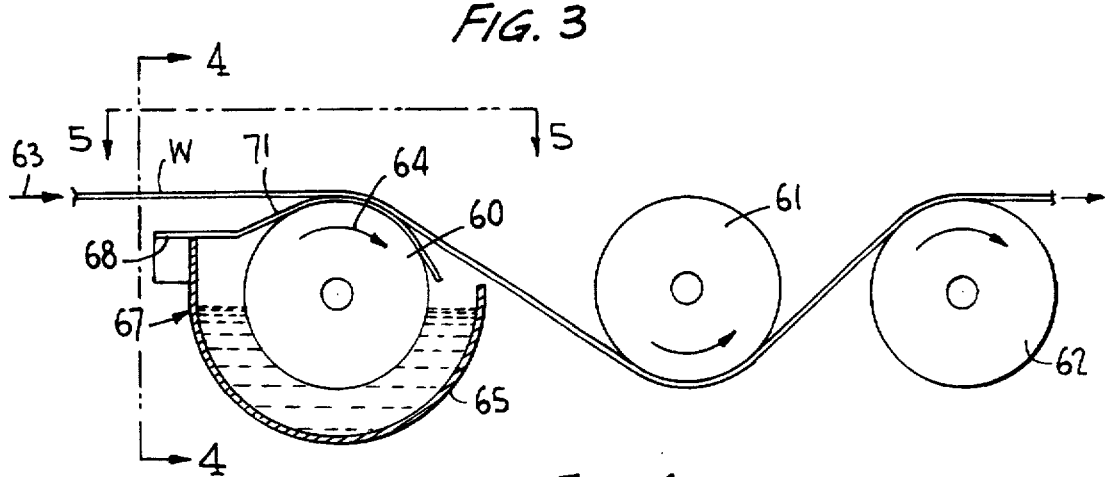
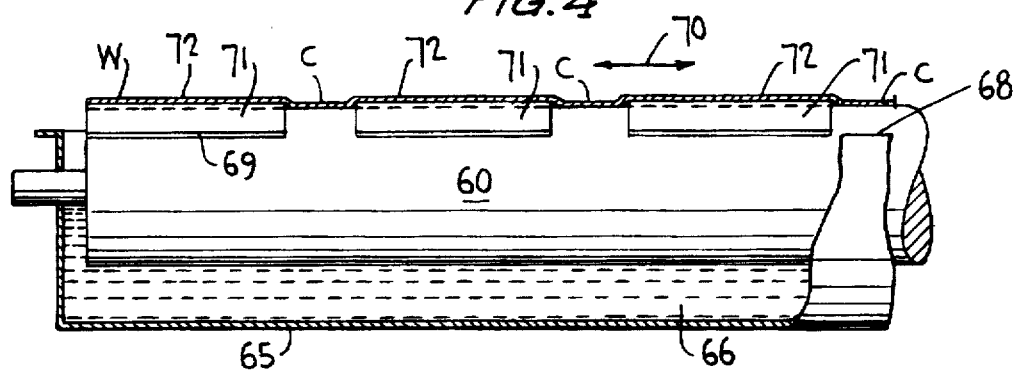
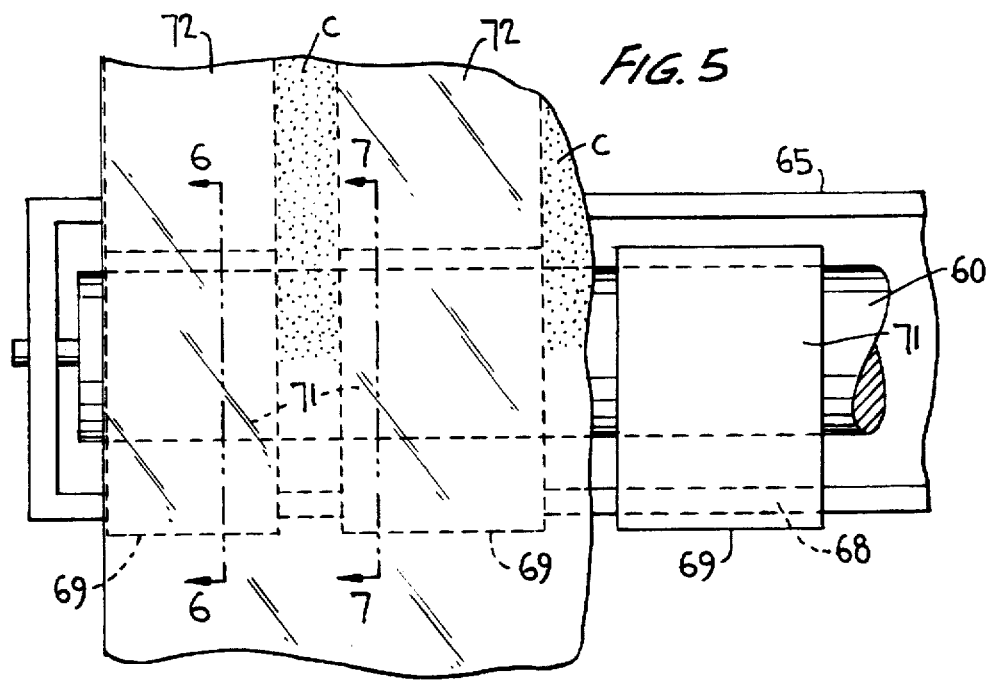

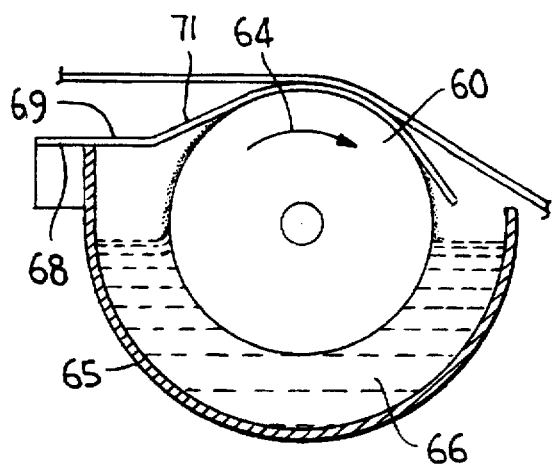
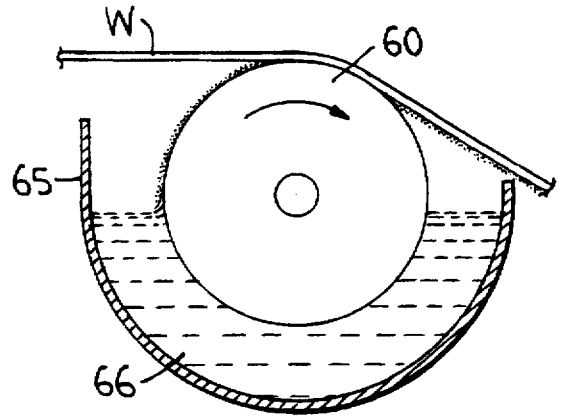
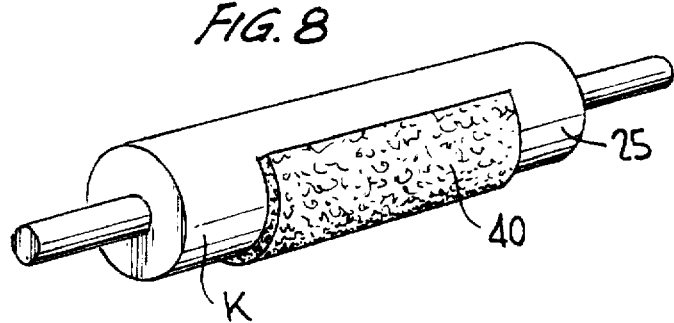
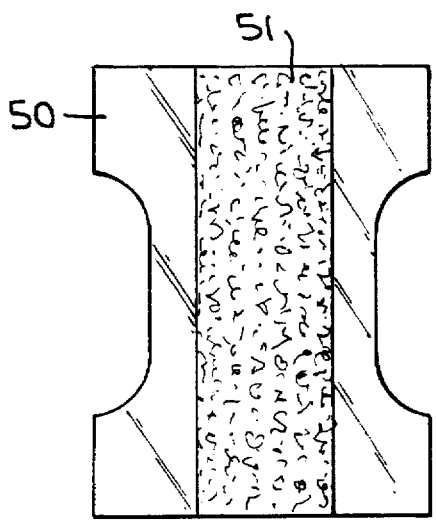
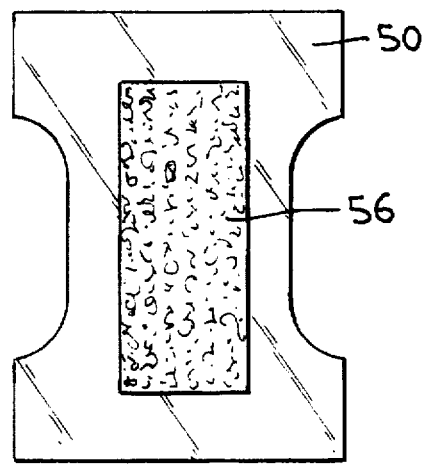

COATING SELECTIVE ZONES OF THIN WEBS TO CHANGE THE PERVIOUS CHARACTER THEREOF, USING A COVER

This is a Continuation-In-Part Application based upon parent application Ser. No. 08/232,692, filed Apr. 25, 1994, now abandoned.

BACKGROUND OF THE INVENTION

It is well-known in the art for the manufacture of disposable baby diapers or other sanitary disposable absorbent products such as sanitary napkins, adult incontinence pads, and hospital bed pads to provide a structure wherein the coversheet or coverstock or top sheet (i.e., that portion of the product which is in contact with the patient's skin) is made of hydrophyllic material so as to be pervious to liquids such as urine. This permits ready pass-through of the liquid into the absorbent core or the pad which lies beneath the coverstock. In the past, some of the coverstocks have also been made of cotton, or blends of cotton and rayon or blends of rayon with a bonding fiber such as polyethylene.

Such coverstock, however, has been undesirable because it tends to retain the moisture and thus feel wet to touch and because it keeps the skin wet and is more likely to cause skin rash or diaper rash or the like.

Therefore, in more recent years, it has been found desirable to use a coverstock made of hydrophobic fibers or filaments, such as polypropylene or polyester, either carded, spun-bonded or melt-blown, or the like, but because such material inherently tends to interfere with the pass-through of urine into the absorbent pad, it has been found necessary to treat the web with a hydrophyllicity-inducing material (surfactant) such as Triton X-102 distributed by Rohm & Haas Co. of Philadelphia, Pa., or MAGNASOFT manufactured by the Union Carbide Company.

The surfactant usually is incorporated with the fibers by the fiber manufacturers before being sent to the web manufacturer, who form a web which is substantially uniformly hydrophyllic. A web thus formed when used as the top sheet in a baby or adult diaper is then coated in areas where perviousness is not only unnecessary but also undesirable. In a more recent form of diaper construction, a strip of nonwoven web of hydrophyllic material is assembled side-by-side between two strips or webs of hydrophobic fibers. When such a 3-strip web is placed upon a diaper, with the pervious strip in the longitudinal center of the diaper, the urine can pass to the absorbent core through the center strip but not along the sides where the coverstock is impervious. However, such a pre-formed, web assembled from three different materials is costly to make and more difficult to run on a diaper machine because of the seam-lines between the hydrophyllic and hydrophobic strips.

In order to overcome such deficiencies, this invention provides a process for applying a coating material to a one-piece hydrophobic web only where the coating is desired.

Such a process is different from a padding process which applies a liquid, such as an adhesive, to an unbonded web of fibers (to create an integrated nonwoven web).

The prior art fails to teach the unique process of the present invention to produce a one-piece web with precisely-located coating zones.

SUMMARY OF THE INVENTION

In the present invention, there is provided a process and apparatus for unwinding a pre-formed well-integrated web of woven or nonwoven, hydrophobic or hydrophyllic fibers and treating the web to create coverstock or top sheet sheets for baby diapers or other similar sanitary disposable absorbent products, such as sanitary napkins, adult products and the like. The web is fed across a roll which rotates in a bath of hydrophyllicity-inducing (or hydrophobicity-inducing liquid, depending on whether the web is basically hydrophobic or hydrophyllic) to apply the liquid to selective areas of the web. The web then is passed through means for insuring that the web is well impregnated, and through a drying system so as to dry or cure the liquid. The treated web is wound in a roll which is subsequently used on a diaper-making machine.

OBJECTS OF THE INVENTION

One object of the present invention is to provide a new process and apparatus for the application of surfactant substances to a web of nonwoven hydrophobic material so as to make selected areas of the web hydrophyllic.

Another object is to provide a process and apparatus for applying hydrophobicity-inducing materials to selected areas of a web of hydrophyllic material so as to render the selected areas impervious to the passage of liquids.

Another object is to provide a one-piece web which has selected liquid-pervious areas for the coverstock of sanitary, disposable absorbent products.

Another object is to provide an apparatus and process which modifies the liquid-pervious characteristics of a wide web of material in a plurality of selected relatively narrow zones, and which apparatus can be easily adjusted to change the width of the relatively pervious zone.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the several instrumentalities of which the invention consists can be variously arranged an organized, and that the invention is not limited to the precise arrangements and organizations of the instrumentalities as herein shown and described.

In the drawings, wherein like reference characters indicate like parts:

FIG. 1 is a schematic diagram of one form of apparatus and process for producing the web of the present invention.

FIG. 2 represents a reproduction of the surface of a hydrophobic web material which has areas treated to render it hydrophyllic, showing how the hydrophobic areas repel liquid while the hydrophyllic areas permit the liquid to pass through.

FIG. 3 is a schematic diagram, similar to FIG. 1, but showing a preferred apparatus and process of the present invention.

FIG. 4 is a cross-sectional view taken along line 4—4 of FIG. 3.

FIG. 5 is a top plan view of the applicator roll taken generally along lines 5—5 of FIG. 3.

FIG. 6 is a view similar to FIG. 4 taken generally along line 6—6 of FIG. 5.

FIG. 7 is a view similar to FIG. 6 taken along line 7—7 of FIG. 5.

FIG. 8 is a perspective view of an applicator roll with a raised liquid-applying portion.

FIG. 9 is a plan view of a baby diaper with a full-length strip of pervious area in the center of the topsheet.

FIG. 10 is a plan view similar to FIG. 9 with an intermittent strip of pervious area in the center of the topsheet.

Figures 1, 2:
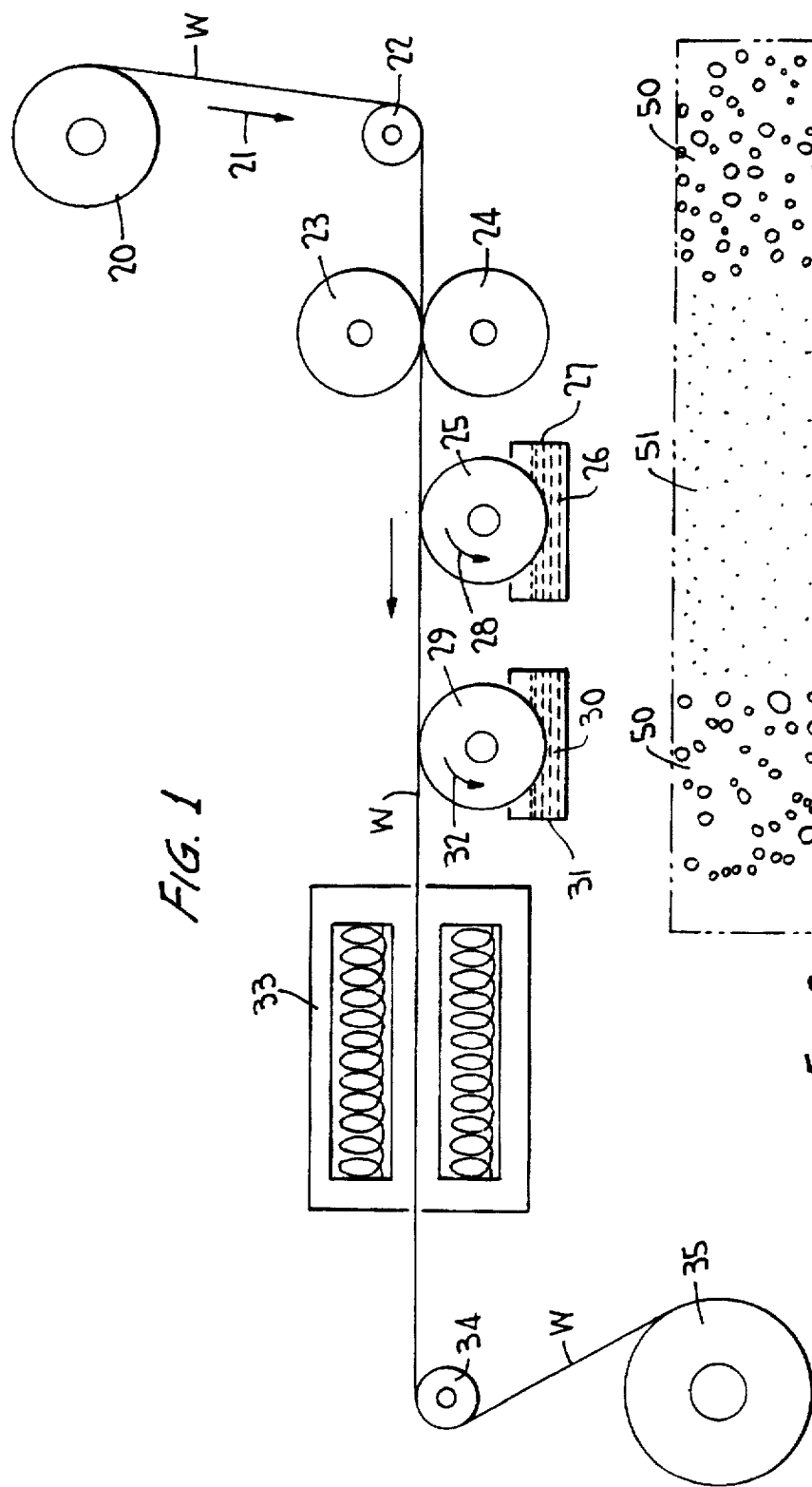

Referring now to FIG. 1, there is shown a pre-formed, well-integrated roll 20 of nonwoven (or woven) coverstock material W which is unwound in the direction of the arrow 21, turning around a carrier roll 22 so that it can pass between rolls 23 and 24 which comprise a set of press or calender rolls.

Thereafter the web passes over a first "kiss" or "padding" roll 25 which applies a selected material 26 from a pan or holder 27 when the roll 25 rotates within the material 26 in the direction of the arrow 28. The material may be either a surfactant, such as TRITON X-102 or MAGNASOFT (if the web is hydrophobic in character) or a material such as products Y-12717 made by OSI Specialists of Switzerland, which induces hydrophobicity (if the web is hydrophyllic).

If desirable, a second roll 29 can be used, also rotating in a bath 30 of material held within a pan 31 and rotating in the direction of the arrow 32 to apply a second coating. This second coating may be of the same material as applied in the first "kiss" roll or it may be opposite in character and applied in a different area of the web.

Thereafter, the web W passes through a drying chamber 33 and around a turning roll 34 to be rolled up on a winder 35. The winder may be 120 inches wide and may be a combination winder/slitter so that individual rolls of finished coverstock of appropriate width may be produced. Desirable widths presently used in the industry are 15 inches, and on such 15 inch wide webs the central pervious strip may be 5 inches wide with a 5 inch wide strip of impervious material on each side of the central strip.

The application of the material may be continuous so as to provide an uninterrupted treated area (as shown in FIG. 9). This "zebra-like" pattern may be preferred for a variety of reasons, not the least significant of which is ease and economy of operation, even though a small amount of material may be applied in areas where its presence is not critical to the operation of the finished product.

Referring now to FIGS. 3–7 inclusive, there is shown a preferred embodiment of a liquid-applying apparatus of the present invention.

The rolls 60, 61 and 62 replace the rolls 25 and 29 as shown in FIG. 1. The web W moving in the direction of the arrow 63 passes over the top of roll 60 beneath roll 61 and over the top of roll 62.

Roll 60 rotates in the direction of arrow 64, partly submerged in a pan 65 containing the liquid surfactant 66.

As the roll 60 rotates, it picks up on the surface thereof the liquid surfactant which is carried out of the pan 65 and deposited against the web W in the areas C where the web W comes onto contact with the surface of the roll 60. Thus the applicator roll carries a measured quantity of liquid surfactant onto the web W. As the web passes from roll 60 beneath roll 61 to the top of roll 62 the web is under tension and the pressure of roll 61 against the web W insures migration of the liquid into the web.

The roll 61 is a tensioning roll which keeps the web W stretched between the roll 60 and 62 and tightly against the top of roll 60. The tension can be changed, as desired, by moving the roll 61 up or down in the direction of arrow A. The position of the roll 61 also determines how much surface of rolls 60, 61 and 62 is in contact with the web W, thus also insuring control of the migration of the liquid into the web.

In a preferred embodiment the peripheral speed of the roll 61 may be as much as 10 times greater than the linear speed of the web W, so as to insure that the web is well impregnated with the liquid.

After the impregnated web W passes from the roll 62, it moves into drying chambers 33 as previously described.

As can be seen particularly in FIGS. 3 and 4, at the upstream side 67 of the pan 65, there are supported on the upper edge 68 thereof a plurality of movable covers 69. These covers are mounted on the edge 68 in such a way that they can be moved along the edge 68 in the direction of the arrow 70 shown more particularly in FIGS. 4 and 5.

Each cover 69 has a flexible downstream portion 71 which lies draped on top of the surface of the roll 60 and prevents the liquid surfactant 66 from coming into contact with the web W at those portions where the flexible portion 71 is between the web and the surface of the roll 60 (which has the film of liquid thereon).

In the area C between the covers 71, the web W is pulled into contact with the surface of the roll 60 by the tension which is created in the web by the tensioning roll 61 and thus in those areas C, between the covers 71, the web is impregnated with a liquid.

It is to be easily understood that the covers 71 can be of a specific width and particularly dimensioned so that the uncoated web portions 72 may be as wide as desired, and the placement of the covers 71, by sliding them along the upper edge 68 of the pan portion 67, determines the width of the impregnated portions C between the unimpregnated portions 72.

Thus as few or as many of the covers may be utilized and they do not all have to be of the same width. Thus the dimensions of the pervious portion 51 in the final web may be of a dimension as desired by the customer, and the impervious or hydrophobic portions 50 can also be selected to the customer's preference.

Downstream of the dryer member 33, either between the dryer 33 and the turning wheel 34 or between the turning wheel 34 and the windup roll 35, the web may be slit by appropriate slitter knives (not shown) and thus wound up in narrow "doughnut-size" rolls for shipment to the customer.

For the first-mentioned embodiment (shown in FIG. 1) there is used (as shown in FIG. 8), a "kiss" or applicator roll K, (also illustrated at 25 in FIG. 1) which has a raised portion 40 which picks up the material 26 from the carrier pan 27 (or 31). The shape of the raised portion 40 may be chosen to provide the desired area of deposition.

FIG. 10 illustrates how the coating material 56 can be limited to a rectangular area which stops short of the ends of the diaper. This design is easily made by the process and apparatus of FIG. 1.

Although a primary desire is to create a hydrophobic web material treated with a surfactant to render treated areas 51 hydrophyllic, it is to be understood that the reverse is just as possible, namely, that the web can be hydrophyllic in nature and the treated areas 51 can be rendered hydrophobic.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having thus described the invention, what is claimed as new and desired to protect by Letters Patent are the following:

1. Apparatus for coating a web of integrated nonwoven material, said apparatus including:

a cylinder roll a body of liquid material means to rotate said roll which is partially submerged in said body whereby to coat a partially submerged surface of said roll with said liquid material at least one cover having an upper surface and positioned above part of an un-submerged surface of said roll means to guide said web across the upper surface of the cover and into contact with the un-submerged portion of said roll not covered by said cover, whereby to apply said liquid material only to the portion of the web not in contact with the cover.

2. The apparatus of claim 1 including a tensioning roll adjacent said roll for controlling tension in the web as well as to control the contact area of said web with said roll and said roll.

3. The apparatus of claim 1 including means for drying the web and liquid material after passing from the roll.

4. The apparatus of claim 1, wherein said cylinder has an axis, and wherein said at least one cover are movable along a line parallel to said axis.

5. The apparatus of claim 1 including means for controlling the speed of the web and the speed of rotation of the roll so that the linear speed of movement of the web is not the same as the peripheral speed of the surface of the roll.

6. The apparatus of claim 5 wherein the speed controlling means insures that peripheral speed of the roll is at least 10 times greater than the linear speed of the web.

* * * * *

UNITED STATES PATENT AND TRADEMARK OFFICE
CERTIFICATE OF CORRECTION

PATENT NO. : 5,709,747
DATED : January 20, 1998
INVENTOR(S) : Moshe Goldwasser

It is certified that error appears in the above-indentified patent and that said Letters Patent is hereby corrected as shown below:

Claim 1, column 5, line 6, "a cylinder roll," should read -- a roll --,

Claim 2, column 6, line 3, "of said web with said roll" should read -- of said web with said tensioning roll --.

Signed and Sealed this

Twenty-eighth Day of July, 1998

Attest:

BRUCE LEHMAN

*Attesting Officer*  *Commissioner of Patents and Trademarks*